United States Patent [19]

Baccaud et al.

[11] Patent Number: 5,559,437
[45] Date of Patent: Sep. 24, 1996

[54] PROCESS AND DEVICE FOR MAGNETICALLY CHECKING WORN TIRES

[75] Inventors: Armand Baccaud, Epoissotte; Damien Baudrit, Avallon, both of France

[73] Assignee: Pneu Laurent, Avallon, France

[21] Appl. No.: 431,574

[22] Filed: May 1, 1995

[30] Foreign Application Priority Data

May 4, 1994 [FR] France ................... 94 05571

[51] Int. Cl.[6] ............... G01N 27/82; B07C 5/02; B60C 11/24
[52] U.S. Cl. ............ 324/240; 73/146; 209/538; 209/567; 324/226; 324/242; 324/262
[58] Field of Search ................ 324/226, 228, 324/237, 238, 240–242, 262; 73/146; 209/538, 567

[56] References Cited

U.S. PATENT DOCUMENTS

| | | | |
|---|---|---|---|
| 2,788,484 | 4/1957 | Deming | 324/228 |
| 2,970,256 | 1/1961 | Sazynski et al. | 324/240 |
| 3,675,375 | 11/1972 | Enabnit et al. | |
| 3,714,558 | 1/1973 | Swanepoel | 324/225 |
| 4,004,693 | 1/1977 | Tsuji et al. | 324/226 X |
| 5,313,827 | 5/1994 | Yovichin | 73/146 |

FOREIGN PATENT DOCUMENTS

| | | |
|---|---|---|
| 0348624 | 1/1990 | European Pat. Off. . |
| 0580024 | 1/1994 | European Pat. Off. . |
| 3418066 | 11/1985 | Germany . |

*Primary Examiner*—Gerard R. Strecker
*Attorney, Agent, or Firm*—Brumbaugh, Graves, Donohue & Raymond

[57] ABSTRACT

A process and apparatus for the non-destructive checking of the condition of a metal reinforcement element of magnetic material in a tire (11) wherein the metallic reinforcement element is subjected to a magnetic field in order to magnetize it;

relative movement is produced between the metallic reinforcement element of the tire (11) and at least one conductor (31) of a detecting device (30) placed opposite the metallic reinforcement element in such a manner than any variation in magnetization of the element produces an electromotive force in the conductor (31);

the electromotive force is detected in order to obtain information as to the condition of said magnetized metallic reinforcement element.

18 Claims, 5 Drawing Sheets

PROCESS AND DEVICE FOR MAGNETICALLY CHECKING WORN TIRES

BACKGROUND OF THE INVENTION

The present invention relates to methods and apparatus for checking the condition of worn tires, for instance before their recapping. More particularly, it relates to a method and apparatus for the non-destructive checking of the condition of metallic reinforcement elements of such tires and, in particular, of the tread plies.

When the tread of a tire is worn, it is customary to "recap" it, that it so say to replace the worn tread by a new one. However, this operation is possible only if the mechanical condition of the tire is satisfactory. For this reason, before and during the recapping, one carefully verifies what defects are present in the tires. Depending on the seriousness of these defects, the tires are repaired or discarded.

The metallic reinforcement elements which are incorporated deep within the tire may, in particular, present defects such as ruptures or oxidation. These defects are not always detected by the manual, visual verification conventionally carried out by an operator.

In order to solve this problem, methods of non-destructive verification, based for instance on X-rays, have been proposed. These methods require a relatively lengthy visual analysis of the results, which does not permit their complete automation; furthermore, they require a substantial investment. As a result, these methods of visualization are very rarely used in recapping.

SUMMARY OF THE INVENTION

The object of the present invention is a process and apparatus for the non-destructive verification of the condition of a metallic reinforcement element of worn tires which can be easily automated and is of reduced expense as compared with the previously known methods of visualization.

In the following, it is understood that "metallic reinforcement element" of a tire is the metal reinforcement plies of the crown, or all or part of the carcass ply if it is metallic, or the bead wires or any other metallic reinforcement element which may be used in a tire. In order that it can be checked, said metallic reinforcement element must be made of magnetic material.

The method for the non-destructive verification of the condition of a metallic reinforcement element of magnetic material in a tire is characterized by:

subjecting said metallic reinforcement element to a magnetic field in order to magnetize said element;

creating a relative movement between said metallic reinforcement element of said tire and at least one conductor of a detection device placed opposite said metallic reinforcement element so that any variation in magnetization of said element induces an electromotive force in said conductor;

said electromotive force is detected in order to obtain information as to the condition of said magnetized metallic reinforcement element.

The relative movement between the metallic reinforcement element of the tire and the conductor can be created by rotating the tire around its axis.

It is also advantageous for the relative speed of rotation between the metallic reinforcement element and the conductor to be known precisely and to be preferably constant.

The method of verification in accordance with the invention thus makes use of the fact that any variation in magnetization of the metallic reinforcement element, due in particular to breaks or oxidation of cables, induces an electromotive force in the conductor of the detection device.

In accordance with a variant, at least one characteristic magnitude of the values of the electromotive force induced is calculated and the condition of the metallic reinforcement element is determined by the comparison of said characteristic magnitude with at least one reference magnitude.

The characteristic magnitude may advantageously be the mean-square value of the electromotive forces induced.

In order to characterize the condition of the metallic reinforcement element, an averaging is effected over the entire tire. Thus, global characteristics are used with reference to at least one previously determined magnitude.

In accordance with one particular manner of operation, the condition of the metallic reinforcement element is classified as "bad" when the mean-square value P of the electromotive forces induced is greater than a threshold $S_H$.

In order to determine the value of the threshold $S_H$:

a homogeneous lot of worn tires is used;

for each tire, the above verification test is effected and the parameter P calculated;

the metallic reinforcement element of all the tires is bared and those which are "acceptable" and those which are "bad" are determined;

the threshold $S_H$ is so selected that all the tires having a value of P greater than $S_H$ are classified as "bad".

The method of verification of the invention thus makes it possible, prior to the recapping operations, to determine those worn tires the condition of the metallic reinforcement element of which is bad and which thus cannot be recapped. This results in a substantial gain in productivity.

In accordance with a supplementary manner of operation, a magnitude $N_b$ which is a function of the dispersion of the electromotive forces induced can be used as second characteristic magnitude.

Thus, after having sampled N values of the electromotive forces induced during a relative rotation of the tire with respect to the conductor by at least one revolution with constant speed of rotation, the N values obtained are squared, said values are classified in decreasing value, and one calculates:

$$P = \frac{1}{N} \sum_{j=1}^{N} e_j^2,$$

means square value of the electromotive forces induced, $N_b$ such that $$\sum_{j=1}^{Nb} e_j^2 = a \sum_{j=1}^{N} e_j^2,$$

in which $e_j$ is the j-th value of the induced electromotive forces sampled, classified in decreasing value and "a" is a number between 0 and 1, and preferably equal to 0.9.

The condition of the metallic plies is classified as "acceptable" when the mean-square value P of the electromotive forces induced is less than a threshold $S_B$, and said condition is classified as "bad" when said mean-square value P is greater than a threshold $S_H$. When the mean-square value P is between the above two thresholds, the condition of the metallic crown layers is classified as "bad" if the value $N_b$ characteristic of the dispersion of the square values of the electromotive forces induced is greater than a threshold $N_c$.

Finally, in order to determine the value of the thresholds $S_B$, $S_H$ and $N_c$:

a homogeneous lot of worn tires is used;

for each tire, the above verification test is carried out and the parameters P and $N_b$ calculated;

the metallic reinforcement elements of all the tires are bared and those which are "acceptable" and those which are "bad" are determined;

the threshold $S_H$ is so selected that all the tires having a value of P greater $S_H$ are classified as "bad";

the threshold $S_B$ is so selected that all the tires having a value of P less than $S_H$ are classified as "acceptable", the threshold $N_c$ is so selected that, for all or practically all the tires having a value of P between the thresholds $S_B$ and $S_H$ and classified as "bad", one has $N_b > N_c$.

This second method of operation has the advantage of identifying among the tires classified as "acceptable" by the above method of operation, those the defects of which are widely distributed over all of the metallic reinforcement elements, and thus cannot be repaired.

Another object of the invention is an apparatus intended for the carrying out of the above process. This device comprises:

means for subjecting a metallic reinforcement element of the tire to a magnetic field and magnetizing it;

a device for detecting variations in magnetization of said metallic reinforcement element comprising at least one conductor placed opposite said metallic reinforcement element;

means for creating a relative movement between said metallic reinforcement element and said detection device.

The relative movement created between the metallic reinforcement element and the detection device is advantageously a movement of rotation having as axis the axis of revolution of said tire, and the speed of this relative displacement is known precisely and is preferably constant.

In accordance with one particular embodiment, the magnetization means are in fixed position with respect to the detection device and comprise at least a first magnetization coil traversed by a direct electric current and at least one first pole piece, the assembly being placed in the vicinity of the radially outer surface of the tire in such a manner that there is a substantially constant gap between every point of the transverse profile of said metallic reinforcement element adjacent to said magnetization device and the said first pole piece.

The detection device advantageously comprises at least one second detection coil as conductor and at least one second pole piece, they being such that the variations in magnetization of the metallic reinforcement element induce electromotive forces in the second detection coil, the entire detection device being offset circularly by an angle α with respect to the magnetization device relative to the axis of revolution of the tire.

In accordance with another aspect of the device in accordance with the invention, the pole piece of the detection device has the shape of a C, the two ends of the arms of the C having a geometry which is adapted to the transverse profile of the metallic reinforcement element and being arranged parallel to each other in the vicinity of the radially outer surface of the tire in such a manner that the gap is substantially constant between every point of the transverse profiles of said metallic reinforcement element which are adjacent to said ends of the arms of the C and said ends.

Finally, in accordance with a preferred embodiment, the detection device comprises a single detection coil.

DESCRIPTION OF DRAWINGS

One embodiment of the invention will now be described in the particular case of the verification of the condition of the metallic plies of the crown of worn tires which are to be recapped. These metallic plies are made of magnetic material. This example will be described with reference to the accompanying drawings, in which.

DESCRIPTION OF PREFERRED EMBODIMENTS

Figure 1:
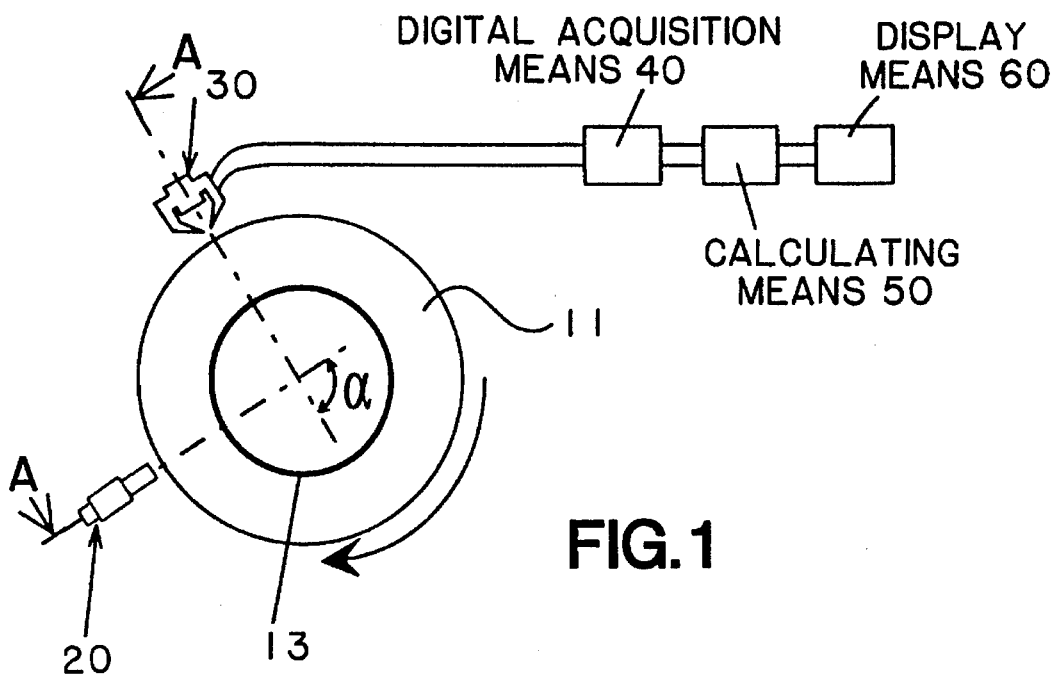
FIG. 1 is an overall diagram of a device for the checking of worn tires in accordance with the invention.
Figure 2:
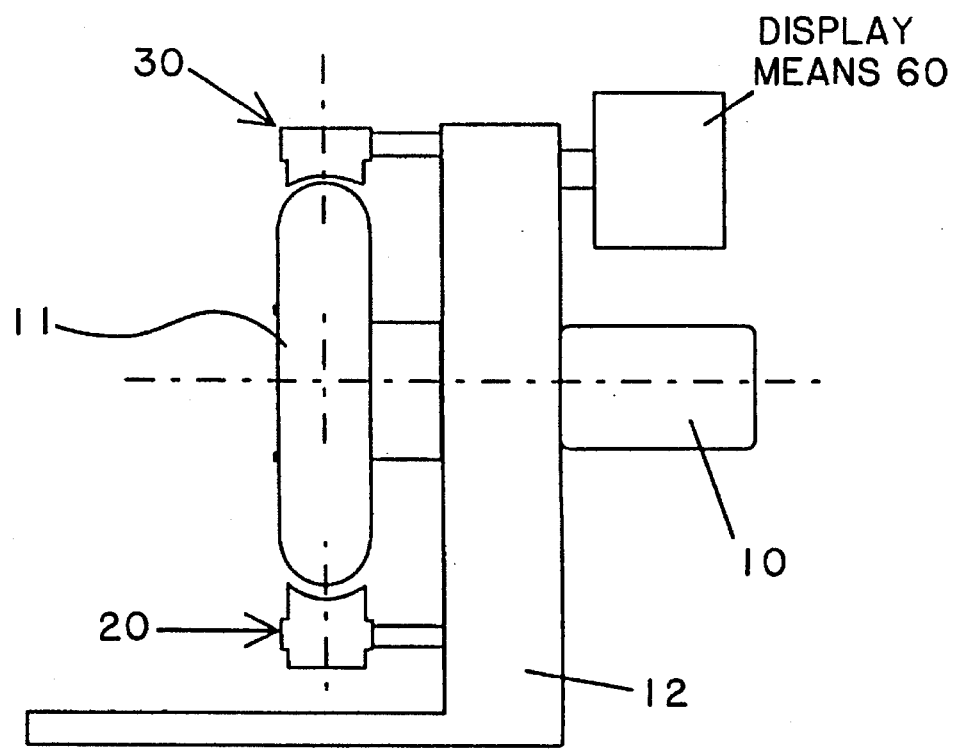
FIG. 2 is a sectional view along the line AA of the device, as indicated in FIG. 1.

FIGS. 1 and 2 show a general diagram of a device for the non-destructive verification of the condition of the crown plies of a worn tire which is to be recapped, in accordance with the invention.

This device comprises means for the holding and rotating of the tire 11 having a frame 12, an expandable mandrel 13 on which the tire 11 is placed before its inflation and before motors 10 is placed in position on the frame, a device 20 supported on the frame for the magnetizing of the metallic reinforcement elements, a device 30 supported on the frame for detecting variations in magnetization of the metallic plies, and finally known digital acquisition means 40, calculating means 50, and display means 60.

The magnetization device 20 and the detection device 30 are arranged circularly apart by an angle α relative to the axis of rotation of the tire 11. This angle is on the order of 90° in the example described.

Figure 3:
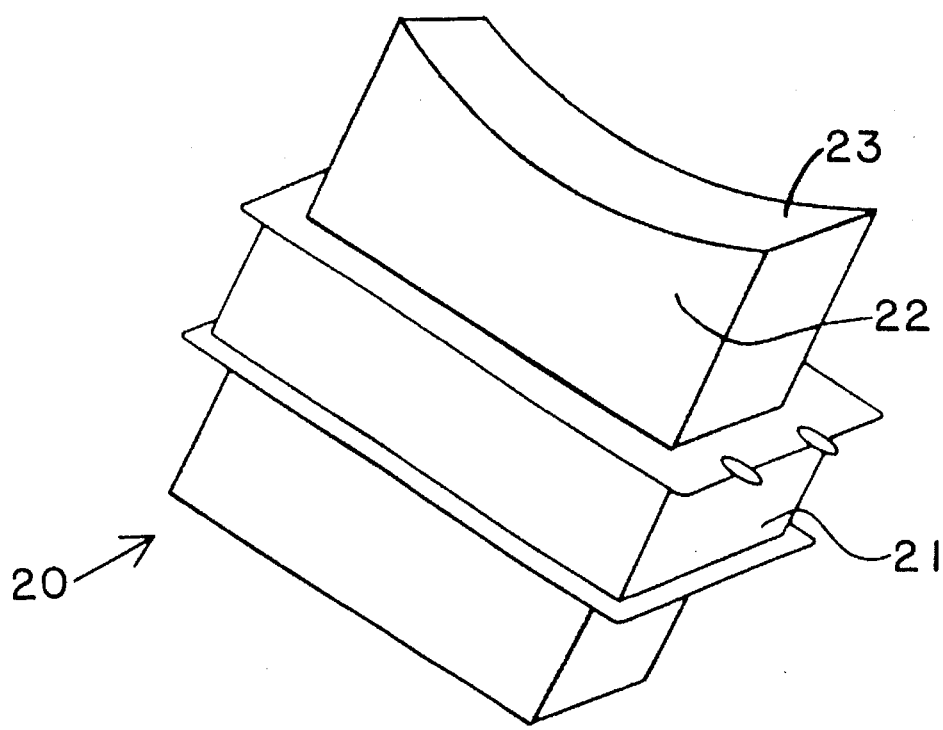
FIG. 3 shows the magnetization device.

FIG. 3 shows the magnetization device 20. This device comprises, in a preferred embodiment, a single coil 21 surrounding a soft-steel pole piece 22. The coil 21 comprises, for instance, 1000 to 1500 turns and is traversed by a direct electric current I of an amperage of 1.2 to 1.5 amps. The pole piece 22 has an outer surface 23 which is generally adapted to the profile of the metallic plies of the crown of the tire 11. The magnetization device 20 (see FIG. 2) is placed opposite the radially outer surface of the crown of the tire 11 in such a manner that there is a relatively constant gap between the transverse profile of the metallic plies adjacent to the device and the surface 23 of the pole piece 22. The value of this gap is such that a tire having a thickness of its tread pattern close to that of a new tire can be tested. In the case of passenger car tires, the gap can be on the order of 12 mm. This gap remains substantially constant during the rotation of the tire 11.

It is not necessary to have a special geometry of the surface 23 for each type of tire.

The coil 21 of the magnetization device 20 can also be replaced by a permanent magnet.

Figure 4:
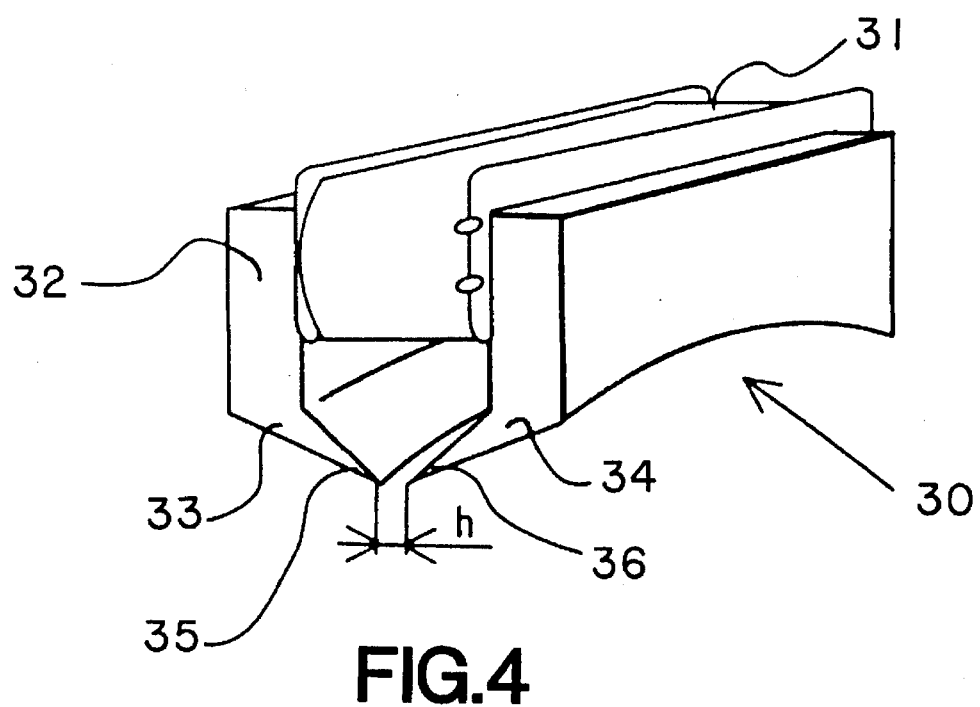
FIG. 4 is a view of the detection device.

The detection device 30 is shown in FIG. 4. In a preferred embodiment, this device comprises a single detection coil 31 and a pole piece 32. This pole piece 32 has the general shape of a C. The coil 31 surrounds the central part of the C. The two arms 33 and 34 of the C extend towards each other. Their ends 35, 36 are separated by a constant distance h. Furthermore, transversely, these ends 35, 36 have a geometry which is adapted to the transverse profile of the metallic reinforcement elements of the tire 11 to be tested. The detection device 30 (see FIG. 2) is placed opposite the radially outer surface of the crown of the tire 11 in such a manner that there is a substantially constant gap between the transverse profiles of the metallic plies adjacent to the device 30 and the ends 35, 36 of the pole piece 32. The value of this gap is also on the order of 12 mm in the case of passenger car tires. It is important for the reliability of the results obtained that the value of this gap be constant. Therefore, it is desirable to have sets of pole pieces 32 for all the types of tires tested.

The detection device 30 must be sensitive to very small variations in magnetization of the metallic reinforcement elements in order to have excellent longitudinal selectivity. Therefore, as conductor 31 in which the electromotive forces are induced there is frequently selected a detection coil 31 having a large number of turns, for instance 20,000 to 40,000, and the distance h separating the two ends 35 and 36 of the pole piece 32 must be as small as possible. A good compromise corresponds to a value for h of about 3 mm.

The speed of rotation of the tire relative to the magnetization and detection devices is preferably constant during the acquisition of the electromotive force values since the value of the electromotive forces induced is proportional to the speed of relative displacement. A variable speed drive device can also be used, provided that the relative speeds are known precisely and are taken into account in the evaluation of the electromotive forces recorded.

In accordance with a first embodiment, the method of verifying the condition of the metallic reinforcement elements of a tire 11 in accordance with the invention comprises the following steps:

the tire 11 to be tested is mounted on the mandrel 13, inflated, and driven in rotation at constant speed, for instance of the order of 120 rpm;

the feed coil 21 being traversed by a direct current I, the magnetic field which it produces magnetizes the metallic reinforcement elements;

the variations in magnetization of the metallic plies create induced electromotive forces in the detection coil 31 via the pole piece 32, which forces are recorded by means of the digital acquisition device 40; this acquisition is effected during a full number of rotations of the tire 11; an acquisition during a single revolution is entirely satisfactory;

the values $e_j$ are then squared and the magnitude P calculated, it being the mean-square value of the electromotive forces;

the condition of the metallic plies is determined by comparison of the value of P with a reference threshold $S_H$; every tire tested for which P is greater than $S_H$ is classified as "bad", the other tires are classified as "acceptable";

the calculation means 50 transmit the result of the classification, namely tire "acceptable" or tire "bad", to the display means 60.

The determination of the reference threshold $S_H$ is effected in the following manner:

a homogeneous lot (same manufacturer, type, dimensions) of tires to be recapped. for instance 70 to 100 worn tires, is used;

for each tire, the verification test in accordance with the invention is carried, and one calculates the parameter $$P = \frac{1}{N} \sum_{j=1}^{N} e_j^2,$$

the mean-square value of the electromotive forces induced;

all the tires are then decapped, that is to say the metallic plies of their crowns are bared by means, for instance, of a decapping knife; one can precisely determine the condition of their metallic crown plies and thus know those which are "acceptable", that is to say those the metallic plies of which have no defects or the defects of which can be repaired, as well as those which are to be classified as "bad";

the threshold $S_H$ is selected in such a manner that all the tires having a value of P of more than $S_H$ are classified as "bad".

In accordance with a supplementary manner of operation, a magnitude $N_b$ which is a function of the dispersion of the electromotive forces induced can be used as second characteristic magnitude.

Thus, after having sampled the electromotive forces induced during a rotation of the tire by at least one revolution at constant speed of rotation, the N values obtained are squared, said values are classified by decreasing value, and one calculates in addition to P:

$N_b$ such that $$\sum_{j=1}^{Nb} e_j^2 = a \sum_{j=1}^{N} e_j^2,$$

in which $e_j$ is the j-th value of the induced electromotive forces sampled, classified by decreasing value, and "a" is a number between 0 and 1, and preferably equal to 0.9.

$N_b$ is a characterization of the dispersion of the values of the electromotive forces induced. The lower its value for a given value of P, the greater the dispersion of the measurements, which corresponds to more punctiform defects of the metallic reinforcement elements in the longitudinal direction of the tire.

The condition of the metallic plies can be classified as "acceptable" when the mean-square value P of the electromotive forces induced is less than a threshold $S_B$, and be classified as "bad" when P is greater than a threshold $S_H$. When P is between the above two thresholds, the condition of the metallic crown plies is classified as "bad" if the value $N_b$ characteristic of the dispersion of the square values of the electromotive forces induced is greater than a threshold $N_c$.

In order to determine the value of the thresholds $S_B$, $S_H$ and $N_c$:

a homogeneous lot, as previously, of worn tires to be recapped is used;

for each tire, the verification test in accordance with the invention is carried out and the parameters P and $N_b$ calculated;

the tread is removed from all the tires and those which are "acceptable" and those "bad" are determined;

the threshold $S_H$ is so selected that all the tires having a value of P of more than $S_H$ are classified as "bad";

the threshold $S_B$ is so selected that all the tires having a value of P less than $S_B$ are classified as "acceptable";

between the two thresholds, the applicant has found that, with due consideration of the various strict requirements concerning permissible repairs, the "acceptable" tires could be distinguished from the "bad" tires as a function of the punctiform or diffuse appearance of the defects. In fact, for the same value of P, a punctiform distribution of the defects corresponds to defects which can easily be noted and repaired; the tire can thus be classified as "acceptable" since it can be repaired; on the other hand, a diffuse distribution of the defects corresponds to numerous small defects which are difficult to note and in any event not capable of repair, economically speaking, while they may constitute a serious risk for the further reliability of the recapped tire, for instance in the event of extensive oxidation of the metallic reinforcement elements. Therefore, one can select a threshold $N_c$ such that for all or practically all the tires classified as "acceptable", one has:

$N_b \leq N_c$ and such that for all or practically all the tires classified as "bad" one has $N_b > N_c$.

This second manner of operation has the advantage of identifying among the tires having a value of P of between the two thresholds $S_H$ and $S_B$ those the defects of which are widely distributed over all of the metallic reinforcement elements and can thus not be repaired or, in any event, are difficult to repair, economically speaking.

Figure 5:
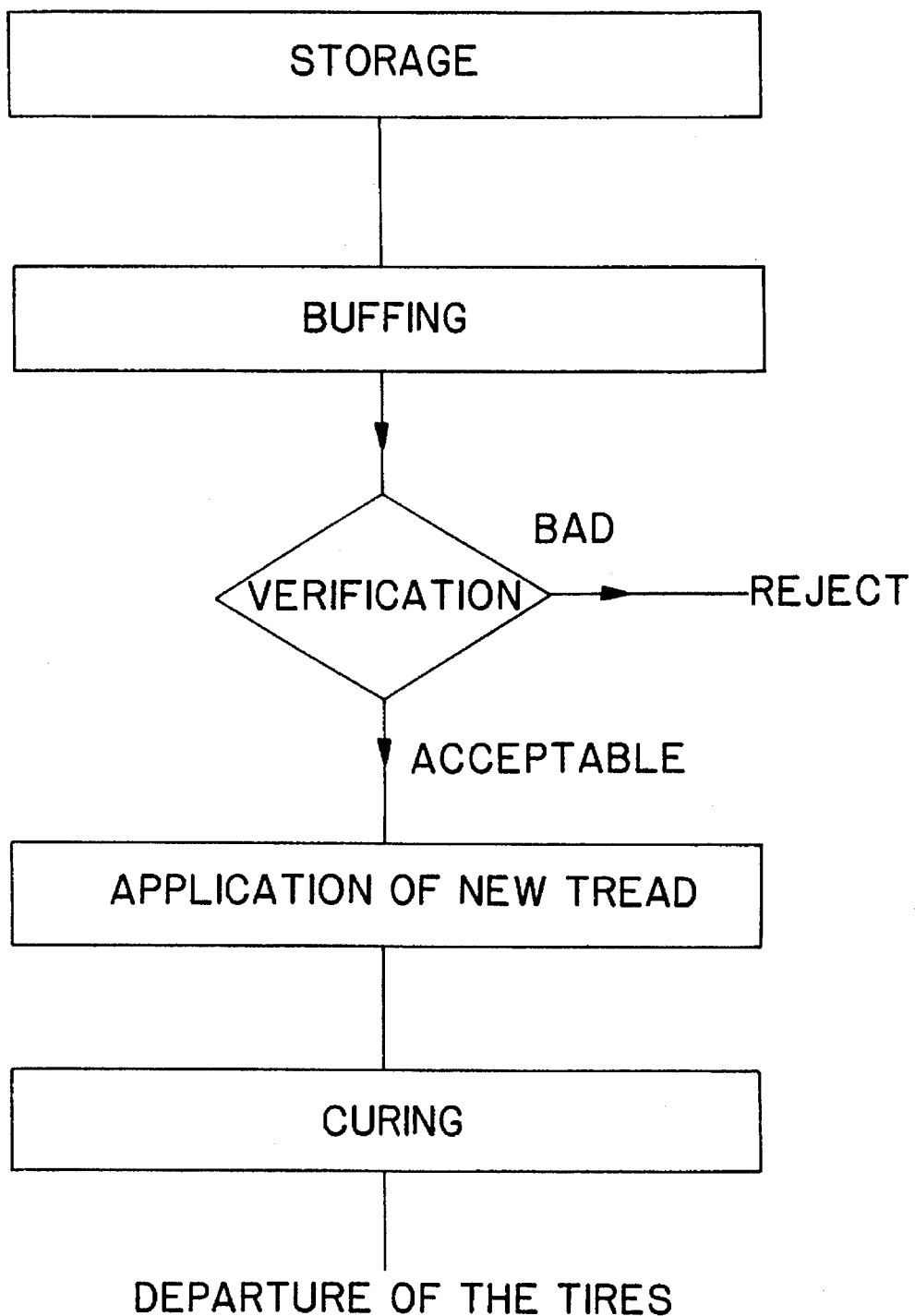
FIG. 5 indicates the steps conventionally employed upon the recapping of worn tires.

The traditional procedure upon the recapping of tires is shown in FIG. 5:

the worn tires are stored upon their arrival;

the remaining used tread is taken off by a machining operation known as "buffing";

all the parts of the tire are then checked; in particular, with regard to the crown, whenever the carded surface of the crown appears "abnormal", the metallic plies are bared at this stage by means of a small hard brush in order to determine whether they show a defect and whether such possible defect can be repaired; if repairs are not possible, the tire is classified as "bad" and is discarded; it is during this brushing operation that the main operation of checking the condition of the metallic reinforcement elements is carried out;

a new tread is placed on;

the bond between the new tread and the crown of the tire is vulcanized as well as the new tread, if necessary.

Figure 6:
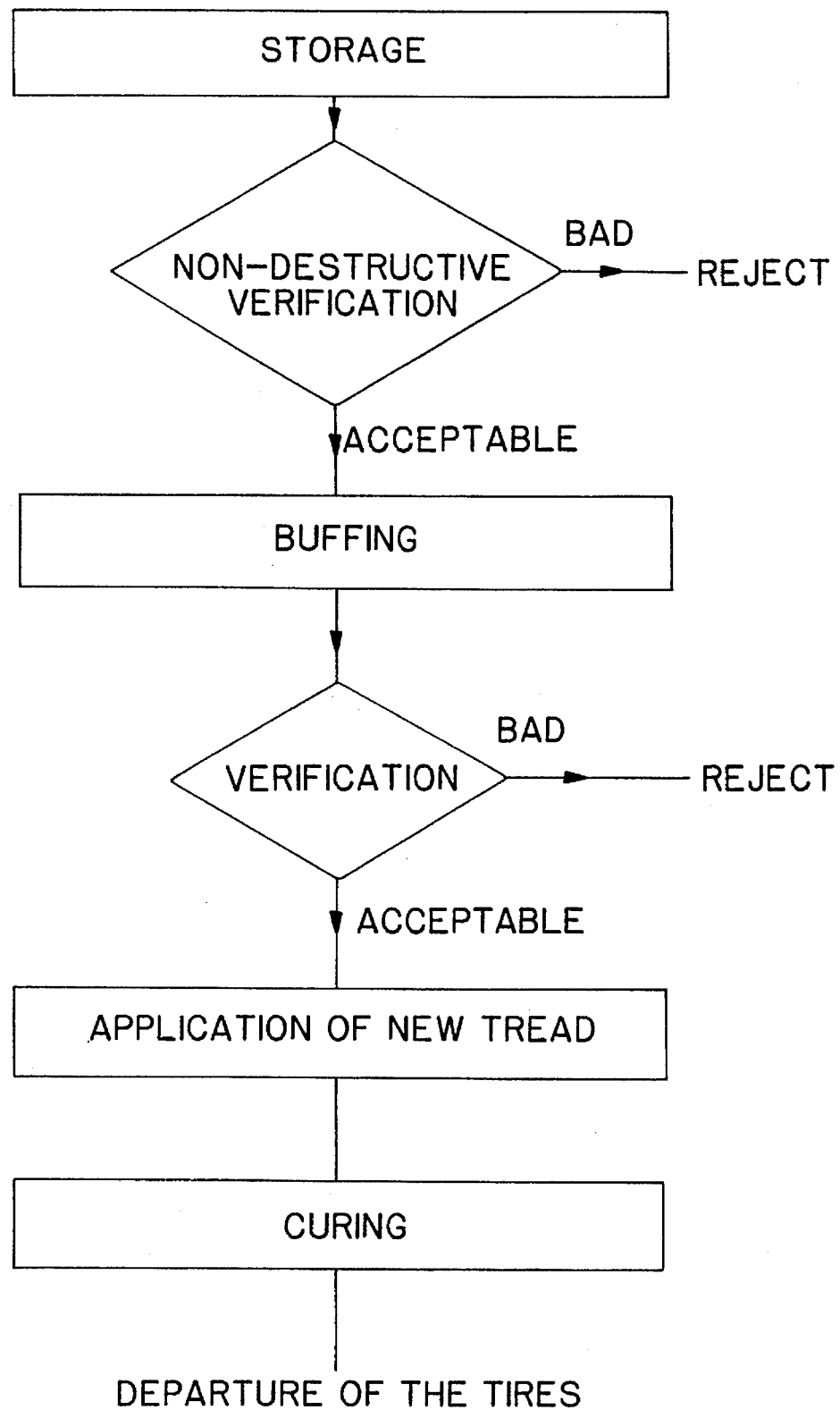
FIG. 6 is similar to the preceding figure and includes the verification in accordance with the invention.

As compared with state of the art, as indicated in FIG. 6, the non-destructive verification operation is carried out before the buffering operation. Accordingly, it is not necessary to effect the buffing operation on tires which are classified as "bad" by this non-destructive verification, this resulting in a gain in productivity.

Another substantial advantage of the invention is that this process makes it possible reliably to identify tires which are very dangerous due to diffuse pockets of oxidation which are very difficult to note upon the brushing. There is therefore a gain in assurance of quality.

The verification device of the invention is of substantially lower cost than X-ray installations, and it is completely automatable. This device can thus be more easily introduced into a recapping shop.

Figure 7:
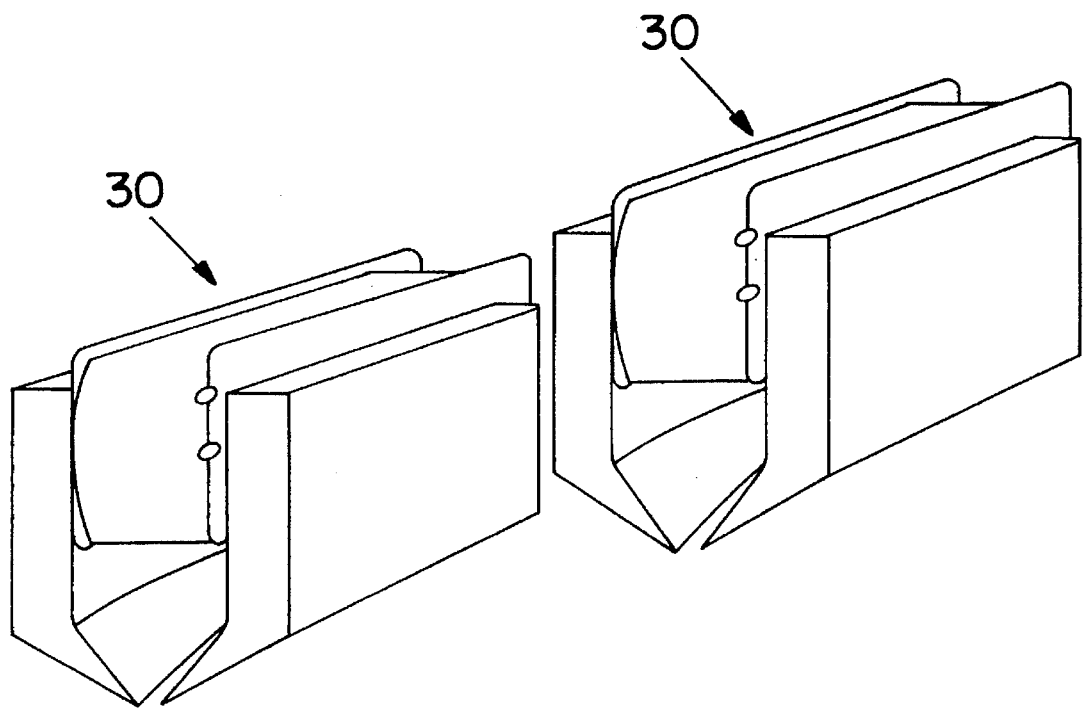
FIG. 7 is a schematic drawing illustrating an alternative embodiment in which a pair of detection devices is provided.

The detection device described above comprises only a single detection coil and thus assures a weighting of the induced electromotive forces over the transverse profile of the metallic plies. Of course, this device and the method of verification described can be extended to the event that several detection coils are used (see FIG. 7), for instance in order more precisely to analyze this or that part of the metallic reinforcement elements.

The method and the device for verifying the condition of the metallic reinforcement elements of worn tires in accordance with the invention are particularly useful prior to the recapping of the tires. However, they can also be applied in other circumstances, such as upon the technical check-up of the vehicles.

We claim:

1. A process for the non-destructive verification of the condition of a metallic reinforcement element of magnetic material in a worn tire, comprising the steps of:

subjecting said metallic reinforcement element to a magnetic field in order to magnetize it;

creating a relative movement between said metallic reinforcement element of said tire and at least one conductor of a detection device placed opposite said metallic reinforcement element in such a manner that any variation in magnetization of said element induces an electromotive force in said conductor;

detecting and recording said electromotive force for the whole of said metallic reinforcement element;

determining at least one magnitude characteristic of the whole of the recorded values of said electromotive forces; and comparing said characteristic magnitude with at lest one reference magnitude in order to determine the condition of said metallic reinforcement element in said worn tire.

2. A process according to claim 1, wherein the relative movement between said metallic reinforcement element of said tire and said conductor is created by the rotating of the tire around its axis.

3. A process according to claim 2, wherein the relative speed of rotation is constant.

4. A process according to claim 1, wherein a mean-square value P is used as characteristic magnitude of said induced electromotive forces.

5. A process according to claim 4, wherein the condition of the metallic reinforcement element is classified as "bad" when the mean-square value P of the induced electromotive forces is greater than a threshold $S_H$.

6. A process according to claim 5, wherein, in order to determine the value of the threshold $S_H$:

a homogeneous lot of worn tires is used;

for each tire, the verification test according to claim 4 is carried out and the parameter P calculated;

the metallic reinforcement element of all the tires is bared and those which are "acceptable" and those which are "bad" are determined;

the threshold $S_H$ is so selected that all the tires having a value P of more than $S_H$ are classified as "bad".

7. A process according to claim 4, wherein, as second characteristic magnitude, a magnitude $N_b$ which is a function of the dispersion of said induced electromotive forces is used.

8. A process according to claim 7, wherein, after having sampled N values of the electromotive forces induced during a relative rotation of the tire with respect to the conductor by at least one revolution at constant speed of rotation, the N values obtained are squared, said values are classified in decreasing value and there is calculated:

P, mean-square value of the electromotive forces induced;

$N_b$ such that $$\sum_{j=1}^{Nb} e_j^2 = a \sum_{j=1}^{N} e_j^2,$$

in which $e_j$ is the j-th value of the sampled induced electromotive forces, classified in decreasing value, and "a" is a number between 0 and 1.

9. A process according to claim 8, such that "a" is equal to 0.9.

10. A process according to claim 7, wherein the condition of the metallic reinforcement element is classified as "acceptable" when the mean-square value P of the induced electromotive forces is less than the threshold $S_B$ and said condition is classified as "bad" when said mean-square value P is greater than a threshold $S_H$, and wherein, when said mean-square value P lies between the two preceding thresholds, said condition of the metallic reinforcement element is classified as "bad" if the value $N_b$ characteristic of the dispersion of the square values of the electromotive forces induced is greater than a threshold $N_c$.

11. A process according to claim 10, wherein in order to determine the values of the thresholds $S_B$, $S_H$ and $N_c$:

a homogeneous lot of worn tires is used;

for each tire a verification test is carried out and the parameters P and $N_b$ are calculated;

the metallic reinforcement element of all the tires is bared and those which are "acceptable" and those which are "bad" are determined;

the threshold $S_H$ is so selected that all the tires having a value of P greater than $S_H$ are classified as "bad";

the threshold $S_B$ is so selected that all the tires having a value of P less than $S_B$ are classified as "acceptable";

the threshold $N_c$ is so selected that for all or practically all the tires having a value of P of between the thresholds $S_B$ and $S_H$ and classified as "bad", one has $N_b > N_c$.

12. A non-destructive device for verifying the condition of a metallic reinforcement element of a tire comprising:

means for subjecting said metallic reinforcement element to a magnetic field and magnetizing it;

a device for detecting variations in magnetization of said metallic reinforcement element which includes at least one conductor placed opposite said metallic reinforcement element for detecting variations in magnetization of said metallic reinforcement element;

means for creating a relative movement between said metallic reinforcement element and said detection device;

means for recording said variations detected by said conductor; and means for determining at least one magnitude characteristic of the whole of the recorded variations for comparison with a reference magnitude to determine the condition of said metallic reinforcement element.

13. A device according to claim 12, wherein the relative movement created between the metallic reinforcement element and the detection device is a movement of rotation around an axis identical with the axis of revolution of said tire.

14. A device according to claim 13, wherein the magnetization means have a fixed position with respect to the detection device and the at least one conductor includes at least one magnetization coil traversed by a direct electric current and at least one first pole piece, the assembly of magnetization coil and first pole piece being placed in the vicinity of the radially outer surface of the tire in such a manner that there is a substantially constant gap between every point of a transverse profile of said metallic reinforcement element adjacent to said magnetization device and said first pole piece.

15. A device according to claim 14, wherein the detection device comprises at least one second detection coil and at least one second pole piece such that the variations in magnetization of the metallic reinforcement element induce electromotive forces in the second detection coil, the entire detection device being spaced circularly by an angle α with respect to the magnetization device relative to the axis of revolution of the tire.

16. A device according to claim 14, wherein the pole piece of the detection device has the shape of a C, the two ends of the C having a geometry adapted to the transverse profile of the metallic reinforcement element and being arranged parallel to each other in the vicinity of the radially outer surface of the tire, in such a manner that the gap is substantially constant between every point of the transverse profiles of said metallic reinforcement element which are adjacent said two ends of the C and said ends of the C.

17. A device according to claim 16, wherein the distance between the two ends of the C is on the order of 3 mm.

18. A device according to claim 12, wherein the detection device comprises a single detection coil.

* * * * *